(12) United States Patent
Lagerwall et al.

(10) Patent No.: US 6,222,079 B1
(45) Date of Patent: Apr. 24, 2001

(54) METHOD OF INCREASING CERTAIN ISOMERIC RATIOS IN CHLORINATING SUBSTITUTED BENZENES

(75) Inventors: Dean R. Lagerwall; Pravin M. Khandare; Hang-Chang Bobby Chen, all of Amherst; Mark F. Lechner, Sanborn, all of NY (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

(21) Appl. No.: 09/429,156

(22) Filed: Oct. 28, 1999

(51) Int. Cl.$^7$ .................................................. C07C 17/00
(52) U.S. Cl. ..................... 570/209; 570/206; 570/210; 570/211
(58) Field of Search .................................. 570/206, 210, 570/211, 209

(56) References Cited

U.S. PATENT DOCUMENTS

| 3,692,850 | 9/1972 | Di Bella . |
|---|---|---|
| 4,031,145 | 6/1977 | Di Bella . |
| 4,031,146 | 6/1977 | Di Bella . |
| 4,069,264 | 1/1978 | Lin . |
| 4,827,058 | * 5/1989 | Mais et al. ........................... 570/211 |

FOREIGN PATENT DOCUMENTS

| 0046555 | 3/1982 | (EP) . |
|---|---|---|
| 2545004 | 11/1984 | (FR) . |
| 1490677 | 11/1977 | (GB) . |

* cited by examiner

*Primary Examiner*—Alan Siegel
(74) *Attorney, Agent, or Firm*—Richard D. Fuerle; Anne E. Brookes

(57) ABSTRACT

Disclosed is a method of increasing the percentage of certain isomers made when di or tri-substituted benzenes are chlorinated in the presence of a Friedel-Crafts catalyst. The use of about 0.001 to about 1 wt % a cocatalyst during chlorination alters the isomeric ratio of the product mixture. In particular, the percentage of the 2,5-isomer is increased when said substituted benzene is ortho or meta-substituted, the percentage of the 3,4-isomer is increased when said substituted benzene is para-substituted, and the percentage of the 2,4,5-isomer is increased when said substituted benzene is 2,4-disubstituted, 3,4-disubstituted, or 2,5-disubstituted.

20 Claims, No Drawings

METHOD OF INCREASING CERTAIN ISOMERIC RATIOS IN CHLORINATING SUBSTITUTED BENZENES

This application is related to Ser. No. 09/193,755, filed Nov. 17, 1998 by V. Lesins et al., titled, "Reducing Meta Content of Isomeric Mixtures of Halo Substituted Toluenes," now U.S. Pat. No. 6,130,361. This application is also related to application Ser. No. 09/428,688, filed of even date by V. Lesins et al., titled, "A Method of Making High Purity 2,4- and 3,4-Dichlorotoluene" now U.S. Pat. No. 6,156,945.

BACKGROUND OF THE INVENTION

This invention relates to the use of cocatalysts to enhance the production of particular isomers when di and tri-substituted benzenes are chlorinated. In particular, it relates to the use of cocatalysts to increase the ratio of 3,4-dichlorotoluene (34DCT) to 2,4-dichlorotoluene (24DCT) when parachlorotoluene (PCT) is chlorinated.

34DCT and 24DCT are useful as intermediates in making chemicals such as pharmaceuticals, herbicides, fungicides, insecticides, paint pigments, and polymerization initiators. A mixture of the two isomers can be made without the presence of other DCT isomers by chlorinating pure PCT. The two isomers can then be separated by distillation. Depending upon the particular product being made, it is often desirable to make more of one of the two isomers and less of the other.

SUMMARY OF THE INVENTION

We have discovered that the presence of certain cocatalysts during the chlorination of di and tri-substituted benzenes will alter the ratio of the isomers produced. In particular, when a disubstituted benzene is ortho, meta, or para, the presence of the cocatalyst increases the ratio of the 2,5 isomer, the 2,5-isomer, and the 3,4 isomer, respectively, and, when a trisubstituted benzene is 3,4, 2,4, or 2,5, the cocatalyst increases the ratio of the 2,4,5-isomer.

DESCRIPTION OF THE PREFERRED EMBODIMENTS

The substituted benzenes used in this invention have the general formula:

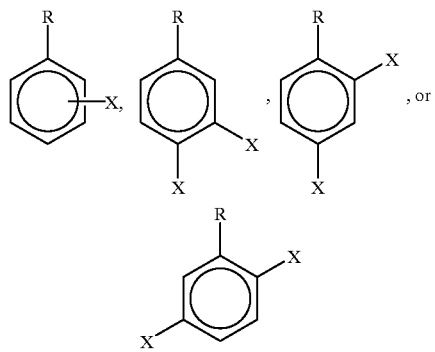

where R is alkyl from $C_1$ to $C_4$ and each X is independently selected from halogen. Preferably, R is methyl, X is chlorine, and the substituted benzene is disubstituted as those compounds are commercially more important. Examples of substituted benzenes that can be used include PCT, o-chlorotoluene (OCT), m-chlorotoluene (MCT), 34DCT, 24DCT, 2,5-dichlorotoluene (25DCT), o, m, and p-chloroethylbenzenes, and o, m, and p-isopropylbenzenes. The preferred substituted benzene is PCT as the products, 24DCT and 34DCT, are commercially important.

About 0.0001 to about 5 wt % of a Friedel-Crafts catalyst (also called a "Lewis acid catalyst") is added to the substituted benzene. Preferably, about 0.001 to about 1 wt % catalyst is used as less is less effective and more is usually unnecessary. Examples of suitable Friedel-Crafts catalysts include the chlorides of manganese, molybdenum, titanium, iron, aluminum, zinc, tin, and antimony, and mixtures thereof, such as ferric chloride, antimony trichloride, antimony pentachloride, thallium trichloride, zirconium tetrachloride, titanium tetrachloride, or a mixture thereof. The catalyst can also be formed in situ as, for example, by adding elemental iron, which reacts with the chlorine to form ferric chloride. The preferred catalyst is ferric chloride as it is inexpensive, works well, and is often the catalyst used to chlorinate toluene to make PCT.

About 0.001 to about 5 wt % of a cocatalyst is used to alter the isomeric ratio of the chlorinated products; less cocatalyst has little effect and more is unnecessary. Preferably, about 0.01 to about 1 wt % of the cocatalyst is used. Examples of suitable cocatalysts include sulfur and sulfur compounds such as diphenylsulfide, disulfur dichloride (also called "sulfur monochloride"), thianthrene, thianthrene derivatives, phenoxathiin, phenoxathiin derivatives, phenothiazine, phenothiazine derivatives, iodine, and iodine compounds. The preferred cocatalysts are thianthrene and thianthrene derivatives, as they are often used in the chlorination of toluene, and disulfur dichloride for its effectiveness.

The isomers that are enhanced by the use of the cocatalyst are as follows (substitutions are relative to the R group):

| | Enhanced Isomer |
|---|---|
| Disubstituted | |
| Ortho | 2, 5 |
| Meta | 2, 5 |
| Para | 3, 4 |
| Trisubstituted | |
| 3, 4 | 2, 4, 5 |
| 2, 4 | 2, 4, 5 |
| 2, 5 | 2, 4, 5 |

The percentage that the enhanced isomer is increased will depend upon the isomer, the cocatalyst, and the chlorination conditions. As an example, a mixture of about 17.3 to about 21.6 wt % 3,4-dichlorotoluene and about 29.5 to about 39.8 wt % 2,4-dichlorotoluene can be made by chlorinating parachlorotoluene using a ferric chloride catalyst and a thianthrene or disulfur dichloride cocatalyst, which is an increase in the ratio of 34DCT to 24DCT from 1 to 3.15 without the cocatalyst to a ratio of 1 to 1.70 with the cocatalyst.

Suitable chlorinating agents include chlorine gas, sulfuryl chloride, and chlorine monooxide. Chlorine gas is preferred as it is inexpensive and easy to control. The amount of chlorinating agent used should be about 0.3 to about 1.5 equivalents (based on the substituted benzene) as less leaves too much unreacted substituted benzene and more can add two chlorines to the ring; the preferred amount is about 0.6 to about 1.0 equivalents.

The preferred procedure is to mix the substituted benzene, the catalyst, and the cocatalyst, heat the mixture, if desired, then sparge in the chlorinating agent. No solvent is needed in this reaction. A temperature range of about 0° C. to reflux can be used for chlorination, but a temperature of ambient to about 90° C. is preferred as the reaction is slower at lower temperatures and at higher temperatures two chlorines may substitute onto the ring. The product mixture can be separated by distillation or other means.

The following examples further illustrate this invention.

EXAMPLES

The monochlorotoluene or dichlorotoluene charge was placed in a reactor equipped with an external heater, a stirrer, a feed inlet, and a gas outlet. The Lewis acid catalyst (or precursor, i.e., Fe°) and the desired amount of chlorinated thianthrene cocatalyst was added and the temperature was raised to 55 to 85° C. Chlorine flow was initiated and the reaction was monitored by gas chromatography (GC). The reaction temperature could be controlled by adjusting the bath temperature and/or the chlorine feed rate.

Examples 1 to 4

OCT

In these examples, OCT was chlorinated. The following table describes the changes in reaction composition (GC area %) resulting from the absence and presence of the cocatalyst at various points in the reaction (TCT=trichlorotoluenes):

|  | Example 1 | Example 2 | Example 3 | Example 4 |
|---|---|---|---|---|
| OCT (g) | 300.54 | 300.00 | 300.54 | 300.00 |
| $FeCl_3$ (g) | 0.183 | 0.184 | 0.183 | 0.184 |
| Cocat (equiv) | — | 3 | — | 3 |
| $Cl_2$ (g) | 100 | 100 | 153 | 150 |
| $Cl_2$ Depth | 0.62 | 0.66 | 0.94 | 0.93 |
| OCT | 42.69 | 37.02 | 18.61 | 15.73 |
| 24DCT | 10.26 | 10.43 | 13.48 | 13.13 |
| 25DCT | 18.31 | 35.34 | 25.15 | 46.06 |
| 26DCT | 15.37 | 6.16 | 19.37 | 7.39 |
| 23DCT | 8.15 | 7.0 | 9.88 | 7.79 |
| TCT | 4.62 | 3.2 | 12.56 | 8.65 |
| 25/Others Ratio | 2.24 | 5.47 | 3.38 | 8.56 |

These examples show that the use of a cocatalyst significantly increased the amount of 25DCT formed when OCT was chlorinated.

Examples 5 to 8

MCT

In these examples, MCT was chlorinated. The following table describes the changes in reaction composition resulting from the absence and presence of the cocatalyst at various points in the reaction:

|  | Example 5 | Example 6 | Example 7 | Example 8 |
|---|---|---|---|---|
| MCT (g) | 300.36 | 300.82 | 300.36 | 300.82 |
| $FeCl_3$ (g) | 0.182 | 0.185 | 0.182 | 0.185 |
| Cocat (equiv) | — | 3 | — | 3 |
| $Cl_2$ (g) | 100 | 100 | 175 | 175 |
| $Cl_2$ Depth | 0.61 | 0.69 | 1.05 | 1.01 |
| MCT | 41.17 | 31.50 | 6.27 | 1.9 |
| 35DCT | 0 | 0 | 0 | 0 |
| 25DCT | 29.34 | 44.71 | 43.95 | 64.4 |
| 34DCT | 11.67 | 16.89 | 15.72 | 22.10 |
| 23DCT | 14.73 | 6.61 | 20.00 | 8.6 |
| TCT | 2.39 | 0.21 | 12.7 | 2.7 |
| 25/Others Ratio | 4.22 | 8.48 | 8.07 | 19.06 |

These examples show that the use of a cocatalyst significantly increased the amount of 25DCT formed when MCT was chlorinated.

Examples 9 to 12

PCT

In these examples, PCT was chlorinated. The following table describes the changes in reaction composition resulting from the absence and presence of the cocatalyst at various points in the reaction:

|  | Example 9 | Example 10 | Example 11 | Example 12 |
|---|---|---|---|---|
| PCT (g) | 300.87 | 301.1 | 300.87 | 301.1 |
| $FeCl_3$ (g) | 0.181 | 0.183 | 0.181 | 0.183 |
| Cocat (equiv) | — | 3 | — | 3 |
| $Cl_2$ (g) | 100 | 106 | 160 | 175 |
| $Cl_2$ Depth | 0.62 | 0.59 | 0.99 | 1.04 |
| PCT | 43.22 | 46.93 | 16.68 | 16.71 |
| 24DCT | 39.20 | 29.51 | 52.62 | 39.84 |
| 34DCT | 12.45 | 17.34 | 15.09 | 21.61 |
| TCT | 5.05 | 6.12 | 15.39 | 21.07 |
| 24/34 Ratio | 3.15 | 1.70 | 3.49 | 1.84 |

These examples show that the use of a cocatalyst significantly increased the amount of 34DCT formed when PCT was chlorinated.

Examples 13 to 16

24DCT and 34DCT

In these examples, 24DCT (Examples 13 and 14) and 34DCT (Examples 15 and 16) were chlorinated. The following table describes the changes in reaction composition resulting from the absence and presence of the cocatalyst at various points in the reaction:

|  | Example 13 | Example 14 | Example 15 | Example 16 |
|---|---|---|---|---|
| 24DCT (g) | 150.65 | 150.56 | — | — |
| 34DCT (g) | — | — | 150.26 | 149.65 |
| Fe ° (g) | 0.016 | 0.015 | 0.018 | 0.015 |
| Cocat (equiv) | — | 2 | — | 2 |
| $Cl_2$ (g) | 65 | 65 | 185 | 185 |
| 24DCT | 26.3 | 23.1 | — | — |
| 34DCT | — | — | 3.5 | 2.4 |
| 234TCT | 16.9 | 14.1 | — | — |
| 245TCT | 35.6 | 53.2 | 51.8 | 66.0 |
| 246TCT | 11.2 | 4.3 | — | — |
| 234TCT and 345TCT | — | — | 31.1 | 23.8 |
| TCTs | 6.6 | 2.7 | 11.3 | 5.1 |

These examples show that the use of a cocatalyst significantly increased the amount of 245TCT formed when 24DCT and 34DCT were chlorinated.

Examples 17 and 18

In these examples, 150 g of a mixture of 89% (GC area) 25DCT, 7.9% 24DCT, and 3.1% 23DCT, 600 ppm (parts by weight per million parts by weight of DCT) elemental iron, 2 equivalents of cocatalyst, and a chlorine depth of 2 was used. The following table gives the GC area % ratio of 245TCT:236TCT:235TCT:

| Example 17 - no cocatalyst | Example 18 - with cocatalyst |
|---|---|
| 40:60:0 | 63:35:2 |

We claim:

1. In a method of chlorinating a substituted benzene having the general formula

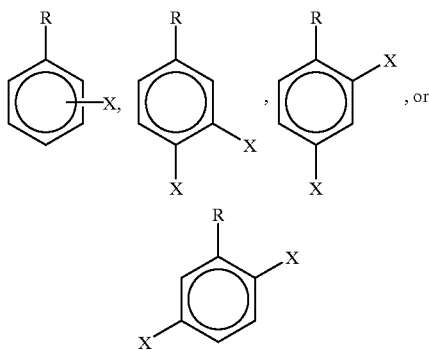

using a Friedel-Crafts catalyst and a chlorinating agent, the improvement comprising chlorinating using about 0.3 to about 1.5 equivalents of a chlorinating agent per equivalent of said substituted benzene in the presence of about 0.001 to about 5 wt % of a cocatalyst selected from the group consisting of thianthrene and thianthrene derivatives, whereby the percentage of the 2,5-isomer is increased when said substituted benzene is ortho or meta-substituted, the percentage of the 3,4-isomer is increased when said substituted benzene is para-substituted, and the percentage of the 2,4,5-isomer is increased when said substituted benzene is 2,4-disubstituted, 3,4-disubstituted, or 2,5-disubstituted, where R is alkyl from $C_1$ to $C_4$ and X is halogen.

2. A method according to claim 1 wherein R is methyl.

3. A method according to claim 1 wherein each X is chlorine.

4. A method according to claim 1 wherein said substituted benzene is disubstituted.

5. A method according to claim 4 wherein said substituted benzene is parachlorotoluene.

6. A method according to claim 1 wherein said Friedel-Crafts catalyst is ferric chloride.

7. A method according to claim 1 wherein the amount of said catalyst is about 0.0001 to about 5 wt %.

8. A method according to claim 1 where said substituted benzene has the general formula

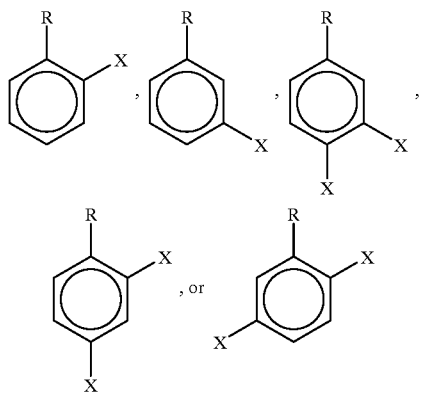

9. A method according to claim 1 wherein said substituted benzene is m-chlorotoluene.

10. A method according to claim 1 wherein said chlorinating agent is chlorine gas.

11. A method according to claim 1 wherein said substituted benzene is orthochlorotoluene.

12. A method according to claim 1 wherein said chlorination is at about 0° C. to reflux.

13. A method of increasing the percentage of 2,5-dichlorotoluene, 2,5-dichlorotoluene, or 3,4-dichlorotoluene, when a substituted benzene selected from the group consisting of o-chlorotoluene, m-chlorotoluene, or p-chlorotoluene, respectively, is chlorinated with about 0.3 to about 1.5 equivalents of chlorine gas in the presence of about 0.001 to about 1 wt % of a Friedel-Crafts catalyst comprising chlorinating in the presence of about 0.001 to about 1 wt % of a cocatalyst selected from the group consisting of thianthrene and thianthrene derivatives.

14. A method according to claim 13 wherein said substituted benzene is parachlorotoluene.

15. A method according to claim 13 wherein said Friedel-Crafts catalyst is ferric chloride.

16. A method according to claim 13 wherein said substituted benzene is o-chlorotoluene.

17. A method according to claim 13 wherein said substituted benzene is m-chlorotoluene.

18. A method according to claim 13 wherein the amount of said chlorinating agent is about 0.6 to about 1.0 equivalents.

19. A method according to claim 13 wherein said chlorinating is performed at about ambient to about 90° C.

20. A method of chlorinating parachlorotoluene to produce a mixture of about 17.3 to about 21.6 wt % 3,4-dichlorotoluene and about 29.5 to about 39.8 wt % 2,4-dichlorotoluene comprising
 (A) adding to said parachlorotoluene
  (1) about 0.1 to about 1 wt % of a catalyst of ferric chloride; and
  (2) about 0.001 to about 1.0 wt % thianthrene;
 (B) heating said parachlorotoluene to a temperature between room temperature and 90° C.; and
 (C) reacting said parachlorotoluene with about 0.6 to about 1.0 equivalents of chlorine gas.

* * * * *